United States Patent
Suchan et al.

(10) Patent No.: US 7,980,852 B2
(45) Date of Patent: Jul. 19, 2011

(54) METHOD AND IMPRESSION TRAY FOR PRODUCING A DENTAL MOLD

(75) Inventors: Matthias Suchan, Hachenburg (DE); Alexander Bublewitz, Herborn (DE)

(73) Assignee: Kettenback GmbH & Co. KG, Eschenburg (DE)

( * ) Notice: Subject to any disclaimer, the term of this patent is extended or adjusted under 35 U.S.C. 154(b) by 607 days.

(21) Appl. No.: 10/549,134

(22) PCT Filed: Jul. 16, 2004

(86) PCT No.: PCT/EP2004/007903
§ 371 (c)(1),
(2), (4) Date: Sep. 15, 2005

(87) PCT Pub. No.: WO2005/046503
PCT Pub. Date: May 26, 2005

(65) Prior Publication Data
US 2006/0269904 A1    Nov. 30, 2006

(30) Foreign Application Priority Data
Oct. 17, 2003   (DE) ................................ 103 49 047

(51) Int. Cl.
*A61C 5/00* (2006.01)
*A61C 19/00* (2006.01)
*A61C 9/00* (2006.01)

(52) U.S. Cl. .............................. 433/215; 433/34; 433/38

(58) Field of Classification Search ................... 433/37, 433/40, 214–215, 48, 213
See application file for complete search history.

(56) References Cited

U.S. PATENT DOCUMENTS

| | | | |
|---|---|---|---|
| 4,968,251 A | 11/1990 | Darnell | |
| 5,031,638 A | 7/1991 | Castaldi | |
| 5,076,791 A | 12/1991 | Madray, Jr. | |
| 5,326,685 A | 7/1994 | Gaglio | |
| 5,415,544 A * | 5/1995 | Oxman et al. | 433/48 |
| 5,582,517 A * | 12/1996 | Adell | 433/6 |
| 5,639,445 A | 6/1997 | Curtis et al. | |
| 5,769,633 A * | 6/1998 | Jacobs et al. | 433/37 |
| 6,247,926 B1 * | 6/2001 | Thornton | 433/48 |
| 6,364,665 B1 * | 4/2002 | Trettenero | 433/215 |
| 2002/0144694 A1 * | 10/2002 | Kittelsen et al. | 128/861 |

FOREIGN PATENT DOCUMENTS

| | | |
|---|---|---|
| DE | 195 11 064 | 9/1996 |
| EP | 0 516 711 | 12/1992 |
| WO | WO 91/12776 | 9/1991 |

\* cited by examiner

*Primary Examiner* — Cris L Rodriguez
*Assistant Examiner* — Heidi M Eide
(74) *Attorney, Agent, or Firm* — McDonnell Boehnen Hulbert & Berghoff

(57) ABSTRACT

The invention relates to a method for producing a dental mold on the basis of a thermoplastic film (4), and to an impression tray (1) for producing such a dental mold (2). The impression tray (1) is charged with a kneadable, malleable material (3) on which the thermoplastic film (4) that can be formed to a dental mold (2) is located. The softening temperature of the thermoplastic film (4) ranges between approximately 40 DEG C and approximately 80 DEG C.

11 Claims, 1 Drawing Sheet

METHOD AND IMPRESSION TRAY FOR PRODUCING A DENTAL MOLD

CROSS REFERENCE TO RELATED APPLICATIONS

Figure 1:
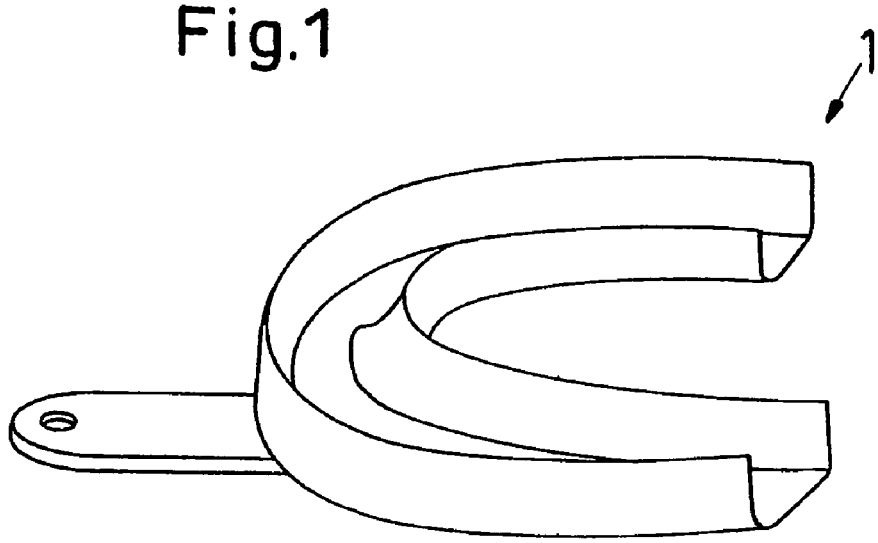

Applicants claim priority under 35 U.S.C. §119 of GERMAN Application No. 103 49 047 filed on Oct. 17, 2003. Applicants also claim priority under 35 U.S.C. §365 of PCT/EP2004/007903 filed on Jul. 16, 2004. The international application under PCT article 21(2) was not published in English.

The invention relates to a method for producing a dental mold, as well as to an impression tray for that purpose, which consists of a material that is solid at temperatures below 140° C., and which is charged with a material that is plastically deformable at least at temperatures between 20° C. and 80° C., preferably between 30° C. and 60° C.

For the treatment of teeth and gums, it is known from U.S. Pat. Nos. 5,639,445 and 5,326,685, for example, to apply active substances by means of a foam-like or sponge-like support material or by means of a plastically deformable support material, which can be laid against a tooth or the gums. Furthermore, U.S. Pat. No. 5,639,445 describes a method for treating teeth or gums, according to which a plastically deformable material is first manually pressed against the teeth or gums, in order to obtain an impression. After one or more active substances is/are applied, this impression can then be applied to the patient's mouth again, for treating the teeth or the gums.

Up to now, dental molds are produced from a thermoplastic film material that is heated over a flame or a heating coil, for example, and placed onto a plaster model produced previously. The film, which is plastically deformable in the heated state, can be adapted to the model by means of a kneadable material, for example, in order to rest against the tooth model as uniformly as possible in this manner. However, by means of being heated over a flame, the film is plasticized to different degrees, and this can result in a non-uniform cover layer of the film and/or in deficient adaptation. Since the film is highly heated over the flame, it is not allowed to come in direct contact with teeth for adaptation, since these could otherwise be damaged. It is therefore necessary to first produce a plaster model, and this is time-consuming and cost-intensive. Heating the film together with the kneadable material is not possible, since the kneadable material is usually not suitable for the temperatures that occur in the case of heating by means of a flame.

Furthermore, a method for producing a bleaching tray is known from U.S. Pat. No. 5,076,791, in which a mouth protector inserted during sports, for example, made of a thermoplastic material, or another suitable carrier is softened in hot water. This mouth protector can be directly adapted to the teeth, in the mouth, using the fingers, in the plastically deformable state. However, because of the non-uniform pressure that is exerted on the tray material with the fingers, it is not possible to achieve a uniform layer thickness and contour fit of the mold. Such bleaching trays are offered for sale under the names "Rapid White" (Natural White GmbH) and "EZNow Tray" (Ultradent Products, Inc.).

U.S. Pat. No. 4,968,251 describes a vacuum deep-drawing method for producing bleaching trays or the like. For this purpose, a film or a plate is heated to a temperature at which it is plastically deformable. In this state, the film or plate is placed onto a plaster model and drawn onto the plaster model by an air-impermeable film, by means of applying a vacuum, so that a tray is produced. At the same time, a sponge-like layer can also be introduced into the tray on the side facing the teeth, using this method. After the tray has cooled down, it, i.e. the sponge-like layer, can be filled with active substances and inserted into the patient's mouth. A device suitable for such a deep-drawing method is disclosed in DE 195 11 064 C2 of Erkodent Erich Kopp GmbH. In the case of this method, as well, a dental impression has to be taken first, and a plaster model of it has to be produced, and this is time-consuming and cost-intensive.

In contrast, it is the task of the present invention to make available a method and an impression tray for producing a dental mold, in order to make available a dental mold with great fit accuracy, at the lowest possible effort and expenditure.

This task is accomplished, according to the invention, with a method that comprises the following steps: Heating a thermoplastic film to a temperature that lies below approximately 80° C. and above the softening temperature of the thermoplastic film, applying the thermoplastic film with an impression tray charged with a kneadable material that is plastically deformable at temperatures between 20° and 80° C., particularly between 30° C. and 60° C., into a patient's mouth, placing the thermoplastic film against at least one tooth, forming a dental mold, for a time span until the thermoplastic film has cooled to a temperature below its softening temperature, and removing the impression tray, the kneadable material, and the dental mold formed from the thermoplastic film from the patient's mouth. Using the method according to the invention, a dental mold can consequently be produced intra-orally, without having to produce a plaster cast. At the same time, by means of the method according to the present invention, a mold having high precision is produced, which can be used, for example, as a bite template, mini-plastic tray, tooth-grinding protector, bandage plate, bite-down tray, bite guide tray, mouth protector, fluoridation tray, bleaching tray, transfer mold and/or positioner. By means of applying the thermoplastic film with the kneadable material, uniform pressure is applied to the thermoplastic film on all sides, so that the dental mold that is produced during cooling and curing demonstrates a uniform layer thickness and contour adaptation. In this connection, the pressure on the thermoplastic film is already produced by the rigid impression tray that is charged with the kneadable material, which in turn lays the thermoplastic film against the teeth. Alternatively or in addition to this, the kneadable material can also be pressed manually against the thermoplastic film, which thereby rests intimately against the teeth. The kneadable material can be a non-curing thermoplastic material such as plastiline, silicone compound, mineral oil compound, or the like, for example, or a chemically curing material such as a conventional two-component molding material, for example.

Preferably, the impression tray, the kneadable material, and the thermoplastic film are jointly heated to a temperature that lies above the softening temperature of the plastic film and below the softening temperature of the impression tray, before being applied to the patient's mouth. The impression tray can consequently be made available as a set, pre-charged with the kneadable material and the thermoplastic film, so that the mold can be produced directly, after the filled impression tray has been heated.

According to another embodiment of the method according to the invention, only the film and the kneadable material can be present in pre-packaged manner, in order to then be jointly introduced into a conventional impression tray, before or after being heated.

Alternatively to this, it is also possible to heat only the thermoplastic film, or the thermoplastic film separately from the impression tray and/or the kneadable material, before application takes place. The time required both for sufficient heating and for cooling during formation of the dental mold can be reduced in this manner.

Preferably, the thermoplastic film is heated to a temperature between approximately 40° C. and 80° C. A processing temperature that is more pleasant for the patient lies between 40° C. and 70° C., particularly between approximately 40° C. and 60° C.

After the dental mold produced from the thermoplastic film has cooled off, it can be removed from the patient's mouth, together with the impression tray and the kneadable material, and subsequently be removed from the kneadable material. However, it is also possible that the mold formed from the thermoplastic film remains in the patient's mouth, at first, while the impression tray and the kneadable material are removed, and that it is only removed afterwards, separately from the impression tray and the kneadable material.

In order to increase the fit accuracy and/or the wearing comfort of the dental mold produced in this manner, it can be trimmed or subsequently finished after having been removed from the patient's mouth.

An impression tray according to the invention, which is suitable for producing a dental mold, consists of a material that is solid at temperatures below 80° C., particularly also at temperatures below 140° C., and is charged with a material that is plastically deformable at least at temperatures between 20° C. and 80° C., preferably between 30° C. and 60° C. In this connection, a thermoplastic film that can be molded into a dental mold, having a layer thickness between 0.1 mm and approximately 4 mm, the softening temperature of which lies between approximately 40° C. and 80° C., is disposed on this plastically deformable material.

Preferably, the layer thickness of the thermoplastically deformable film lies between 0.5 and 3 mm, particularly approximately between 0.5 mm and 2 mm. The films particularly suitable for the method according to the invention and the impression tray according to the invention have a thickness of 0.5 mm, 0.8 mm, 1.0 mm, or 1.5 mm, for example.

According to a preferred embodiment of the invention, the thermoplastic film consists, for example, of copolymer of ethyl acetate and vinyl acetate, polycaprolactone, polypropylene, polyethylene, or a plastic with shape memory. Such materials are available, for example, from DuPont, Solvay, Atofina, and mnemoScience, respectively.

According to the invention, it is provided that the thermoplastic film is provided to be plate-shaped flat or horseshoe-shaped flat and disposed on the kneadable, plastically deformable material. Alternatively to this, it is also possible that the thermoplastic film is disposed on the plastically deformable material in such a manner that it has a U-shaped cross-section. In this connection, the thermoplastic film can also be shaped to be horseshoe-shaped.

The impression tray provided according to the invention is preferably pre-packaged with the plastically deformable material and the thermoplastic film to produce a three-layered set, so that the impression tray can be applied directly after having been heated. However, it is also possible that all or some of the components of the impression tray are present separately from one another, in order to heat the thermoplastic film separately, for example.

The invention will be explained in greater detail below, using exemplary embodiments and making reference to the drawing.

Figure 2:
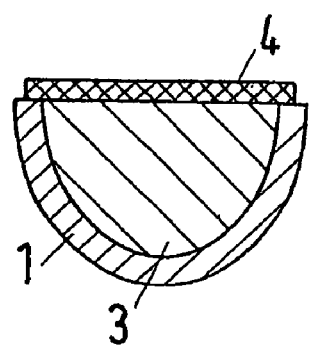
Figure 3:
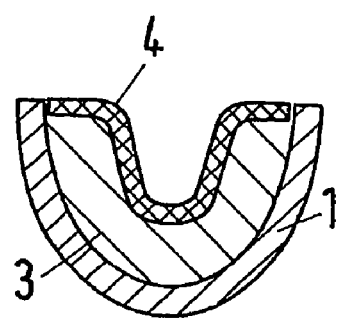
Figure 4:
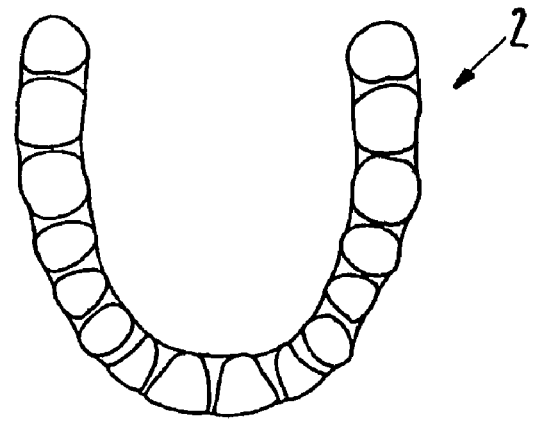

The figures schematically show:

FIG. 1 a perspective view of an unfilled impression tray,

FIG. 2 in cross-section, a filled impression tray according to a first embodiment of the invention, FIG. 3 in cross-section, a filled impression tray according to another embodiment of the invention, and FIG. 4 a top view of a dental mold.

FIG. 1 to 3 show an impression tray 1 that corresponds, for example, to a conventional impression tray for producing a dental mold, from which a plaster model can be produced. The impression tray 1 can consist of metal or plastic, and is rigid at least at temperatures below 80° C., and essentially cannot be deformed manually. If the impression tray 1 is also rigid at temperatures below 140° C., it can be sterilized in an autoclave. The impression tray 1 has a horseshoe shape, generally following the contours of a person's teeth, and has a U-shaped cross-section in the embodiment shown.

In order to produce a dental mold 2 as shown in FIG. 4, the impression tray 1 is filled with a kneadable, plastically deformable material 3, as shown in FIG. 2 and 3. Furthermore, a thermoplastic film 4 is laid onto or into the kneadable material 3. In this connection, the thermoplastic film 4 has a layer thickness between 0.1 mm and approximately 4 mm, for example approximately 0.5 mm to 2 mm. At body temperature and room temperature, the thermoplastic film 4, which can consist, for example, of copolymer of ethyl acetate and vinyl acetate, polycaprolactone, polypropylene, polyethylene, or a plastic with shape memory, is solid. Only at temperatures that lie above body temperature, i.e. between 40° C. and 80° C., does the thermoplastic film 4 become plastically deformable manually. At these temperatures, the kneadable material experiences no or only slight viscosity changes, or can have a tougher consistency in the starting state, and only obtain a kneadable consistency at the processing temperatures that lie above that.

According to the embodiment shown in FIG. 2, the thermoplastic film 4 is configured approximately as a flat plate, which can project beyond the impression tray 1 or can be essentially fitted to the contour of the impression tray 1 and cut into a horseshoe shape. Alternatively to this, it is also possible that the thermoplastic film 4 is inserted into the kneadable material 3 and into the impression tray 1 in such a manner that it is configured to be approximately U-shaped, as shown in FIG. 3.

In order to produce a dental mold 2, the thermoplastic film 4 is heated to a processing temperature that can lie between 40° C. and 60° C., for example. In this connection, either the impression tray 1 together with the kneadable material 3 and the thermoplastic film 4 can be heated in a water bath or the like. Alternatively to this, the thermoplastic film 4 can also be brought to the processing temperature separately from the impression tray 1 and/or the kneadable material 3, and only afterwards be placed onto the impression tray and the kneadable material.

In order to produce a dental mold 2, the thermoplastic film 4 is applied directly to the mouth of a patient. For this purpose, the thermoplastic film 4 is laid onto a row of teeth or individual teeth, separately or together with the impression tray 1 and the kneadable material 3. When the rigid impression tray 1, filled with kneadable material, is pressed against the row of teeth, the thermoplastic film 4 deforms in accordance with the contours of the teeth, whereby the kneadable material 3 exerts a uniform pressure on the thermoplastic film 4 on all sides. As a result, the thermoplastic film 4 experiences no or only very slight changes in its layer thickness, and rests directly against the teeth. In this manner, a dental mold 2 is formed from the plastically deformable film 4, which mold solidifies after cooling to body temperature.

The impression tray 1 can then be removed from the mouth together with the kneadable material 3 and the dental mold 2. In this connection, the materials of the kneadable material 3 and the mold 2 are selected in such a manner that they do not combine with one another at the processing temperature, and can easily be removed from one another. Alternatively to this, the impression tray 1 with the kneadable material 3 can first be removed from the mouth, while the dental mold 2 remains in the mouth and is removed separately.

After any trimming or other subsequent finishing that might be required, the dental mold 2 produced directly in the patient's mouth can be used as a bite template, mini-plastic tray, tooth-grinding protector, bandage plate, bite-down tray, bite guide tray, mouth protector, fluoridation tray, bleaching tray, transfer mold, positioner, or the like.

The invention claimed is:

1. Method for producing a dental mold, comprising the following steps:
    Charging a rigid impression tray (1), which is solid at temperatures below 140° C., with a kneadable material (3), which is plastically deformable at least at temperatures between 20° C. and 80° C., and a thermoplastic film (4), such that said thermoplastic film (4) is horseshoe-shaped and has a U-shaped cross-section that is fitted to a contour of the impression tray and is disposed on said kneadable material (3), wherein the materials of the kneadable material and the thermoplastic film (4) are selected in such a manner that they do not combine with one another at the processing temperature,
    Subsequently heating the thermoplastic film (4) disposed on said kneadable material (3) to a temperature that lies below 80° C. and above the softening temperature of the thermoplastic film (4),
    Applying into a patient's mouth the heated thermoplastic film (4) disposed on said kneadable material (3) in the impression tray (1),
    Placing the thermoplastic film (4) against at least one tooth, forming a dental mold (2), for a time span until the thermoplastic film (4) has cooled to a temperature below its softening temperature, and
    Removing the impression tray (1), the kneadable material (3), and the dental mold (2) formed from the thermoplastic film (4) together from the patient's mouth and removing the dental mold (2) afterwards from the kneadable material (3) and the impression tray (1).

2. Method according to claim 1, wherein the impression tray (1), the kneadable material (3), and the thermoplastic film (4) are jointly heated to a temperature that lies above the softening temperature of the thermoplastic film (4) and below the softening temperature of the impression tray (1), before being applied to the patient's mouth.

3. Method according to claim 2, wherein the thermoplastic film (4) and the kneadable material (3) are introduced into the impression tray (1) together, pre-packaged.

4. Method according to claim 1, wherein the thermoplastic film (4) is heated to a temperature between 40° C. and 60° C.

5. Method according to claim 1, wherein the thermoplastic film (4) is pressed against at least one tooth by the kneadable material (3), to form the dental mold (2).

6. Method according to claim 1, wherein the dental mold (2) is trimmed and/or subsequently finished after having been removed from the patient's mouth.

7. Method according to claim 1, wherein the thermoplastic film (4) is fitted to an outer contour of the impression tray.

8. Method according to claim 1, wherein the thermoplastic film (4) is fitted to an inner contour of the impression tray.

9. Method for producing a dental mold, comprising the following steps:
    Providing an impression tray, which tray consists of a material that is solid at temperatures below 140° C. and which is charged with a material (3) that is plastically deformable at least at temperatures between 40° C. and 80° C., wherein a moldable thermoplastic film (4) having a layer thickness between 0.1 mm and approximately 4 mm, the softening temperature of which lies between approximately 40° C. and 80° C., which can be molded to form a dental mold (2) is disposed on the plastically deformable material (3);
    Heating the thermoplastic film (4) disposed on said kneadable material (3) to a temperature that lies below 80° C. and above the softening temperature of the thermoplastic film (4),
    Applying into a patient's mouth the heated thermoplastic film (4) disposed on said kneadable material (3) in the impression tray (1),
    Placing the thermoplastic film (4) against at least one tooth, forming a dental mold (2), for a time span until the thermoplastic film (4) has cooled to a temperature below its softening temperature, and
    Removing the impression tray (1), the kneadable material (3), and the dental mold (2) formed from the thermoplastic film (4) together from the patient's mouth and removing the dental mold (2) afterwards from the kneadable material (3) and the impression tray (1).

10. Method according to claim 9, wherein the film (4) has a layer thickness of approximately 0.5 mm to approximately 2 mm.

11. Method according to claim 9, wherein the thermoplastic film (4) consists of copolymer of ethyl acetate and vinyl acetate, polycaprolactone, polypropylene, polyethylene, or a plastic with shape memory.

* * * * *

UNITED STATES PATENT AND TRADEMARK OFFICE
CERTIFICATE OF CORRECTION

PATENT NO. : 7,980,852 B2  Page 1 of 1
APPLICATION NO. : 10/549134
DATED : July 19, 2011
INVENTOR(S) : Matthias Suchan et al.

It is certified that error appears in the above-identified patent and that said Letters Patent is hereby corrected as shown below:

At item (73) of the cover sheet:

Please delete "Kettenback GmbH & Co. KG," and replace with "Kettenbach GmbH & Co. KG,"

Signed and Sealed this
Tenth Day of July, 2012

David J. Kappos
*Director of the United States Patent and Trademark Office*